(12) United States Patent
Langton

(10) Patent No.: US 10,583,010 B2
(45) Date of Patent: Mar. 10, 2020

(54) PROSTHETIC HIP ALIGNMENT DEVICE

(71) Applicant: David Langton, Gateshead (GB)

(72) Inventor: David Langton, Gateshead (GB)

( * ) Notice: Subject to any disclaimer, the term of this patent is extended or adjusted under 35 U.S.C. 154(b) by 879 days.

(21) Appl. No.: 14/430,366

(22) PCT Filed: Sep. 23, 2013

(86) PCT No.: PCT/GB2013/052485
§ 371 (c)(1),
(2) Date: Mar. 23, 2015

(87) PCT Pub. No.: WO2014/045064
PCT Pub. Date: Mar. 27, 2014

(65) Prior Publication Data
US 2015/0245914 A1 Sep. 3, 2015

(30) Foreign Application Priority Data
Sep. 21, 2012 (GB) .................. 1216853.0

(51) Int. Cl.
*A61F 2/36* (2006.01)
(52) U.S. Cl.
CPC .... *A61F 2/3609* (2013.01); *A61F 2002/3652* (2013.01)
(58) Field of Classification Search
CPC .................................................. A61F 2/3609
See application file for complete search history.

(56) References Cited

U.S. PATENT DOCUMENTS

| | | | | |
|---|---|---|---|---|
| 2,666,430 A | * | 1/1954 | Gispert | A61B 17/1703 606/96 |
| 5,141,512 A | | 8/1992 | Farmer et al. | |
| 5,672,176 A | * | 9/1997 | Biedermann | A61B 17/7032 606/271 |
| 6,302,890 B1 | * | 10/2001 | Leone, Jr. | A61B 17/1746 606/91 |
| 2002/0058942 A1 | * | 5/2002 | Biedermann | A61B 17/7032 606/308 |
| 2003/0073998 A1 | * | 4/2003 | Pagliuca | A61B 17/0218 606/86 A |
| 2004/0220567 A1 | * | 11/2004 | Eisermann | A61B 17/1642 606/86 A |

(Continued)

FOREIGN PATENT DOCUMENTS

| | | |
|---|---|---|
| EP | 1982676 | 10/2008 |
| WO | 2010128320 | 11/2010 |

OTHER PUBLICATIONS

International Search Report and Written Opinion for related PCT Application No. PCT/GB2013/052485 dated Apr. 7, 2014 (15 pages).

*Primary Examiner* — Jan Christopher L Merene
(74) *Attorney, Agent, or Firm* — Winthrop & Weinstine, P.A.; Nadeem W. Schwen

(57) ABSTRACT

A prosthetic hip alignment apparatus includes a medical instrument (20) comprising a mount attachable to a bone and first (22), second (30), third (40) and fourth (60) members. Adjacent ones of the first, second, third and fourth members are rotatable with respect to each other about a first axis, and between one of the first to fourth members and another means permitting rotation about second and third axes is provided. One of the member mounts a level (64) and wherein one of said members mounts direction indicator (65).

34 Claims, 12 Drawing Sheets

(56) References Cited

U.S. PATENT DOCUMENTS

| | | | | |
|---|---|---|---|---|
| 2005/0273101 | A1* | 12/2005 | Schumacher | A61B 17/7037 606/306 |
| 2006/0293690 | A1* | 12/2006 | Abdelgany | A61B 17/7086 606/103 |
| 2007/0129731 | A1* | 6/2007 | Sicvol | A61B 17/7032 606/104 |
| 2007/0239160 | A1* | 10/2007 | Zipnick | A61B 17/320016 606/86 A |
| 2009/0221879 | A1* | 9/2009 | Gorek | A61B 17/708 600/214 |
| 2010/0082035 | A1* | 4/2010 | Keefer | A61B 17/1746 606/91 |
| 2013/0018430 | A1* | 1/2013 | Murphy | A61B 17/1746 606/86 R |
| 2014/0277198 | A1* | 9/2014 | Stad | A61B 17/7074 606/86 A |

* cited by examiner

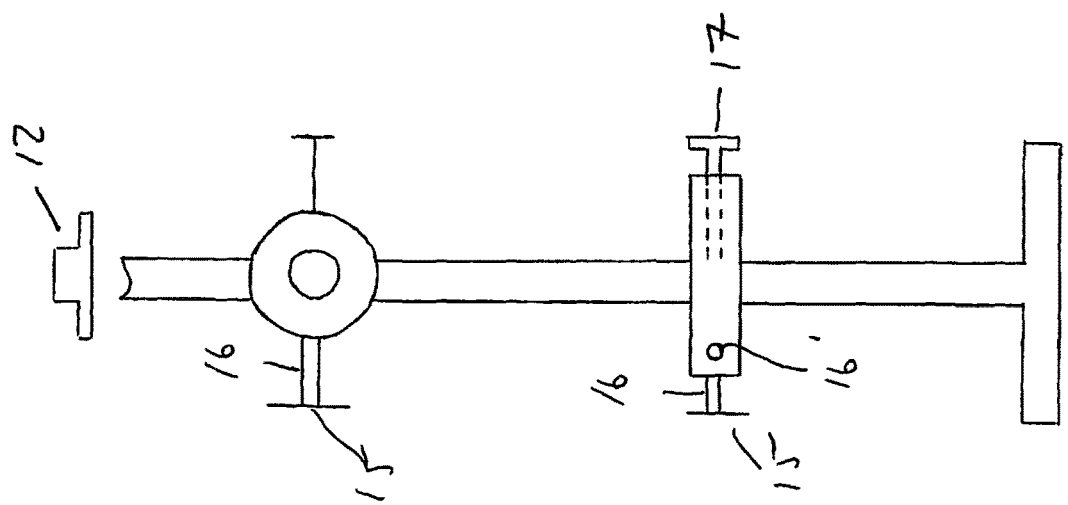
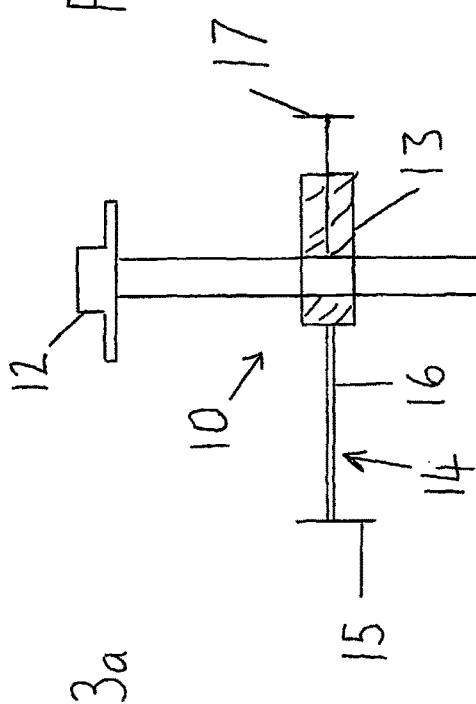
FIGURE 3a
FIGURE 3b

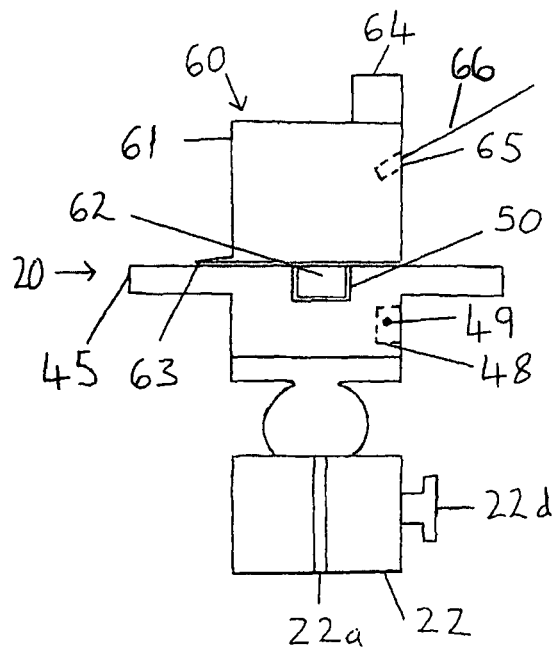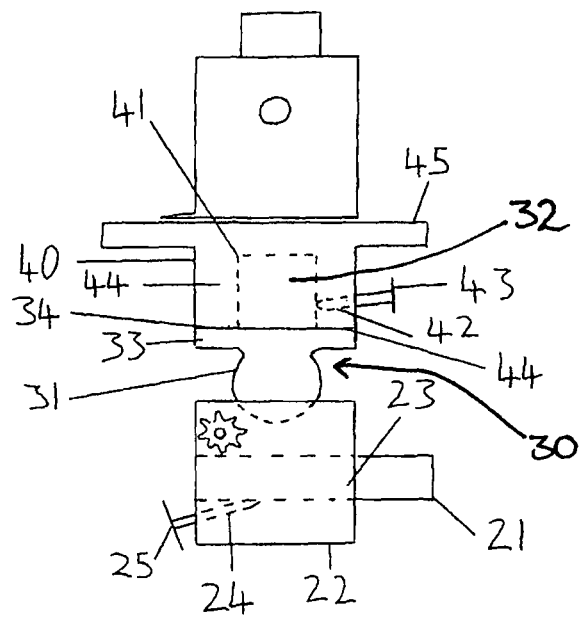
FIGURE 4a
FIGURE 4c
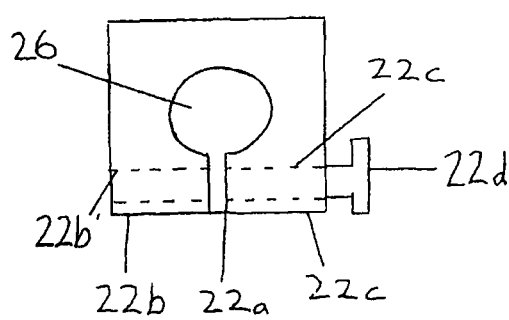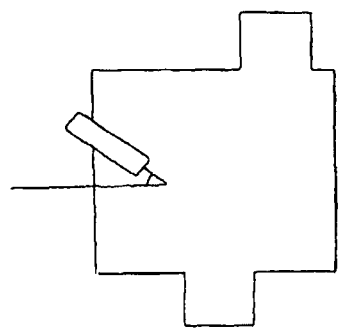
FIGURE 4d
FIGURE 4e

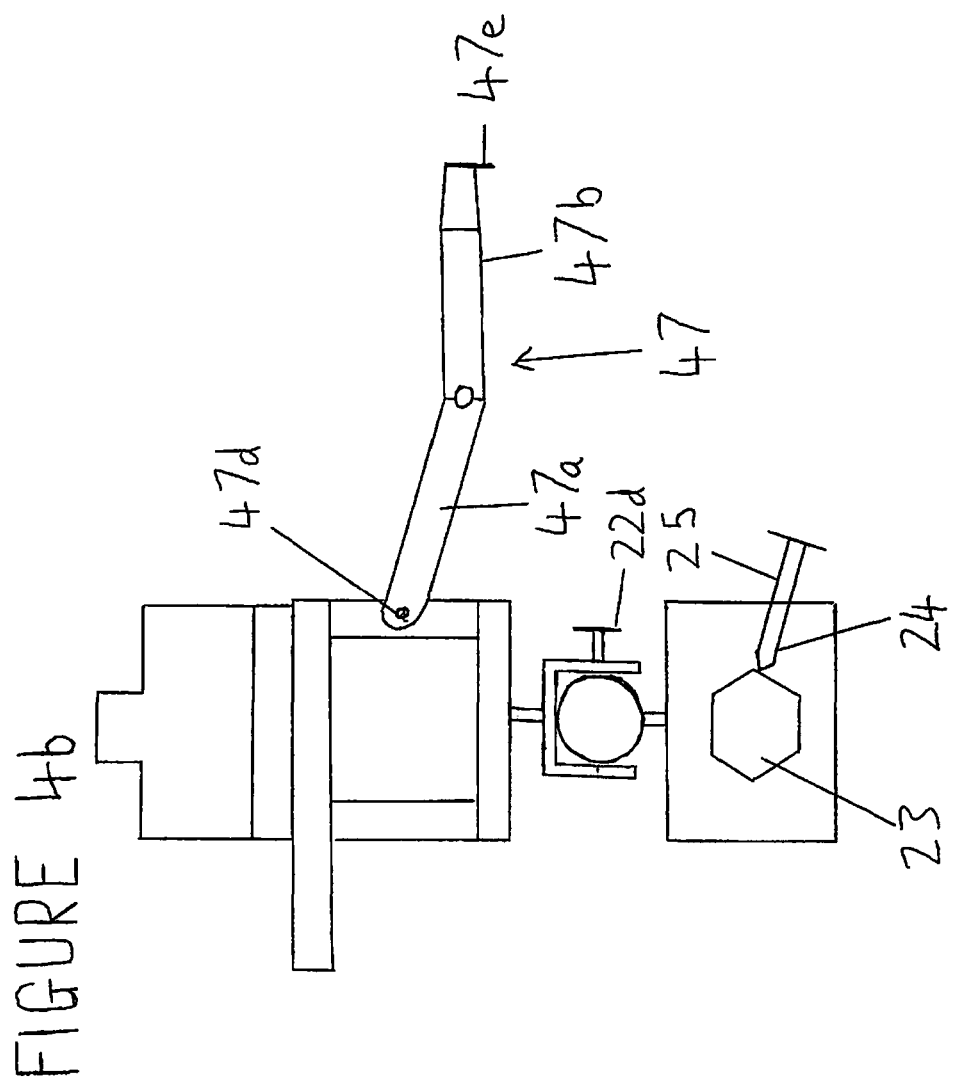

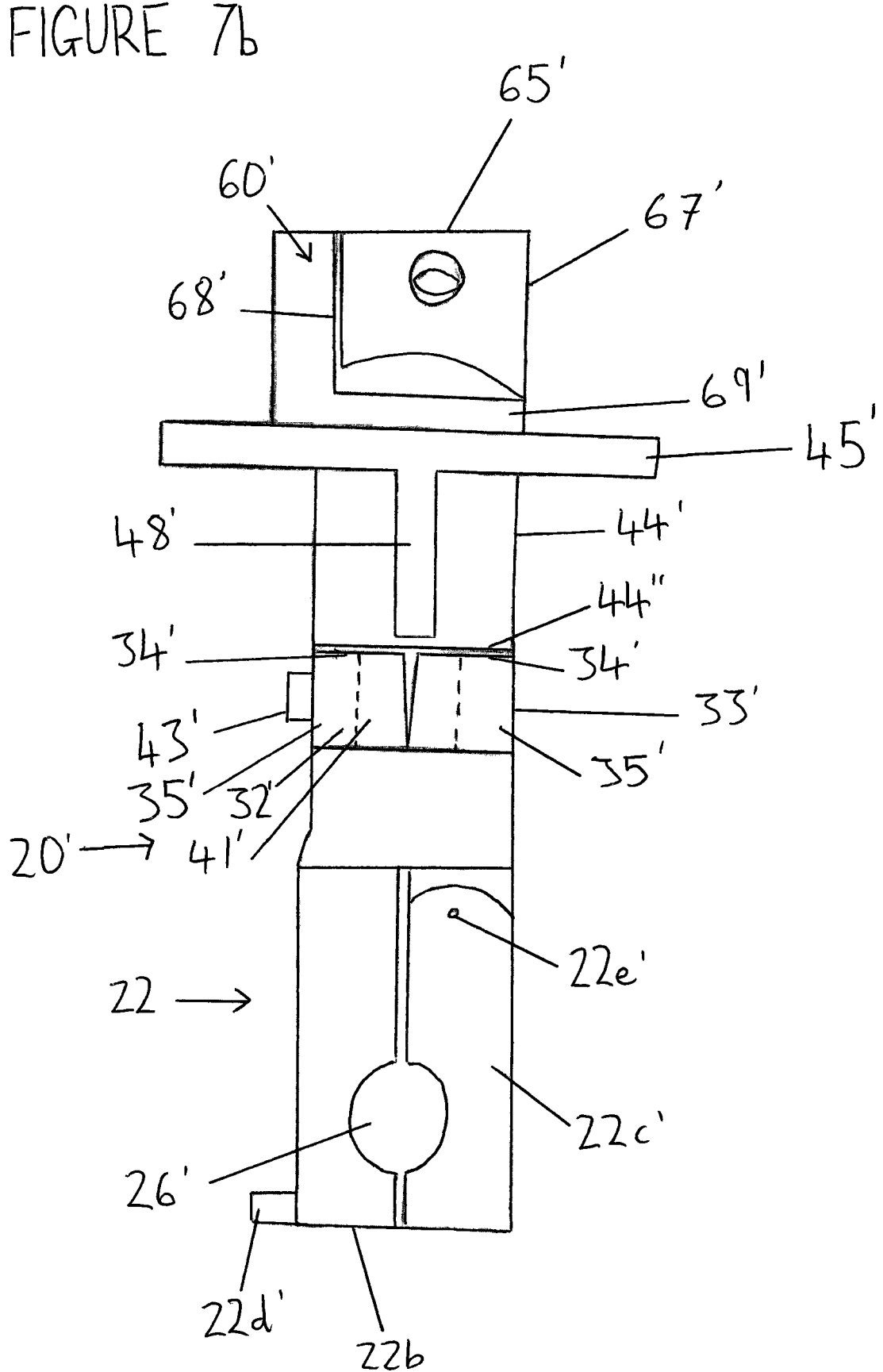

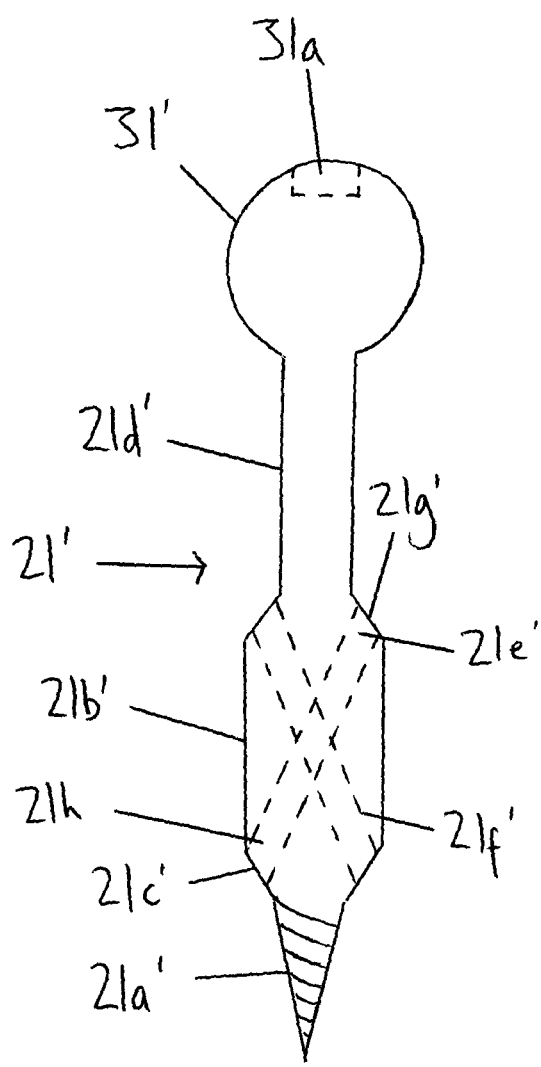
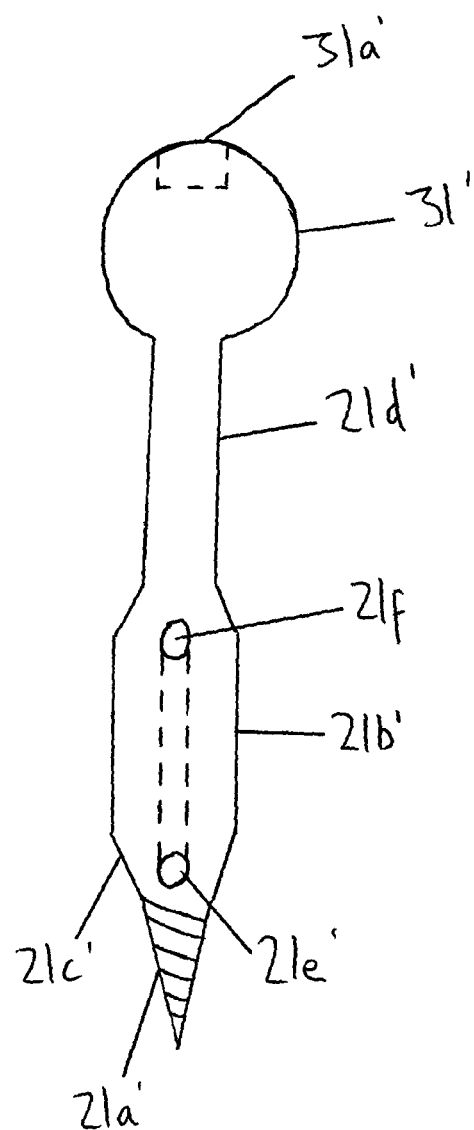

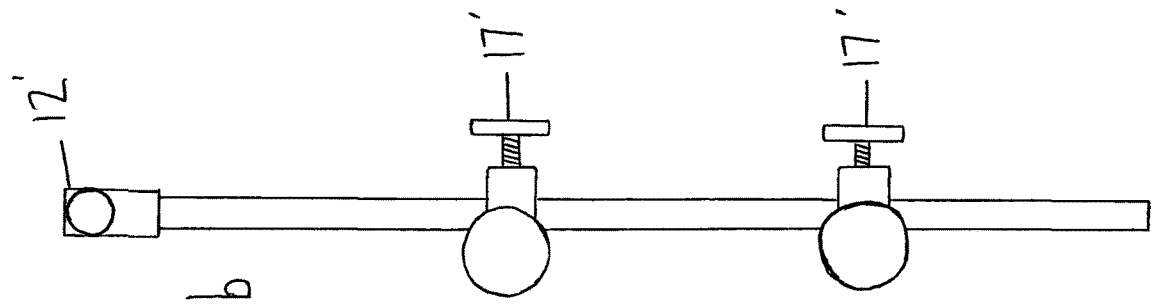
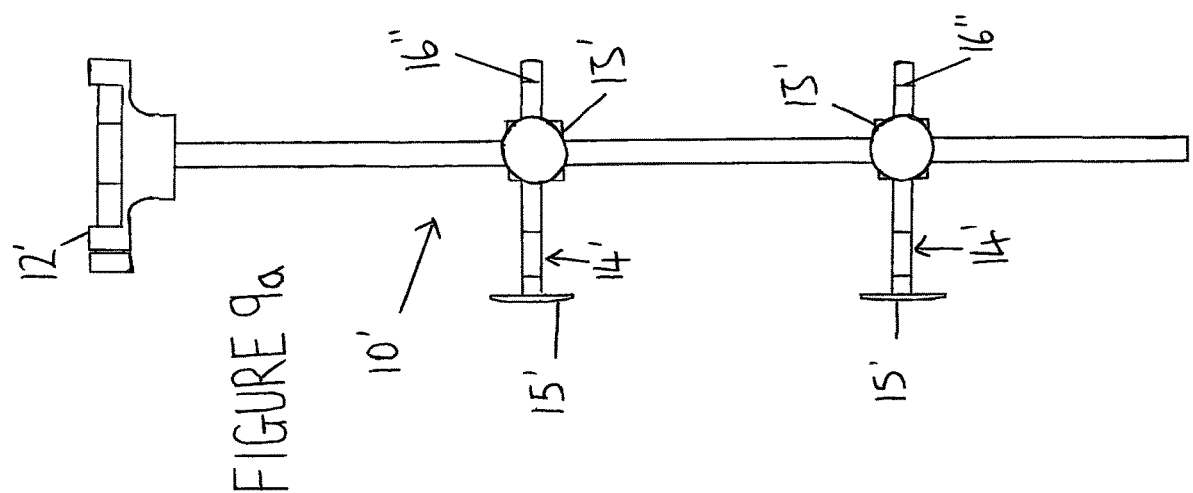

PROSTHETIC HIP ALIGNMENT DEVICE

CROSS-REFERENCE TO RELATED APPLICATIONS

The present application is the U.S. national stage application under 35 U.S.C. § 371 of International Patent Application No. PCT/GB2013/052485, titled "Prosthetic Hip Alignment Device," filed Sep. 23, 2013, and claims the benefit of UK Patent Application No. 1216853.0, filed Sep. 21, 2012, each of which is hereby incorporated by reference herein in its entirety.

FIELD OF THE INVENTION

The present invention relates to an alignment device for use in the alignment of the socket or cup element of a prosthetic hip.

BACKGROUND OF THE INVENTION

Prosthetic hip joints are routinely used to replace a patient's hip joint when that joint is damaged. Many tens of thousands of such hip replacement operations are performed each year around the world.

The prosthetic hip joint typically comprises an acetabular prosthetic socket or cup, which is placed in the hip and a femoral head, which fits into the cup.

It has long since been appreciated that the acetabular cup substituting for the acetabulum has to be inserted into the pelvis in the correct orientation. However, the extent to which the acetabular cup is often incorrectly oriented has only been established in recent years.

The techniques used by orthopaedic surgeons for orienting the prosthetic acetabular cup range from the most basic "eyeballing", where the surgeon uses his experience and orients the cup as he thinks best, with no particular equipment to assist him in establishing that the cup is correctly oriented, to very complex navigation systems, with basic spirit levels and laser beams mounted on the introducer falling in between.

Examples of different navigation systems are described in U.S. Pat. Nos. 5,141,512, 6,711,431 and US 2009/0171370.

U.S. Pat. No. 5,141,512 describes a navigation system including a light source having an angle adjusting element, and three foot portions each fixed to a respective point of the pelvis. An angle adjusting element controls the direction of a light beam emitted from a light source, so that the direction corresponds to the insertion orientation of the prosthetic acetabular cup. This system does not take account of the any change in position of the patient during surgery.

U.S. Pat. No. 6,711,431 describes a system that defines a patient's pelvic plane with reference to at least three pelvic points, and traces a pelvic tracking marker, fixable to the pelvic bone, by using a location tracking device, which tracks the orientation of the pelvic plane in real time. The system can trace the patient's pelvic plane regardless of variation in the patient's pelvic plane position. However, this system is physically large and expensive.

US 2009/0171370 describes a navigation system for the fitting of a prosthetic acetabular cup which includes a mechanism capable of indicating the pelvic plane regardless of variation in the patient's pelvic position during surgery. The mechanism includes a y-shaped member mounting three probes, each of which rests on a different point on the pelvis.

Other simpler devices for assisting the surgeon in orienting the acetabular cup comprise instruments that are mounted on the introducer (the device that is used to force the acetabular cup into the pelvis).

For example, U.S. Pat. No. 6,743,235 describes an introducer that mounts a lever to which are attached a one dimensional spirit level and laser, the spirit level being fixed with respect to the lever and the laser being pivotably mounted on the lever. The spirit level is mounted on the lever such that when the introducer is positioned with its longitudinal axis aligned at 45 degrees to the horizontal, the spirit level is horizontal. The surgeon uses the laser to guide him in adjusting the extent of antiversion of the prosthetic acetabular cup by aligning the laser beam with respect to the acetabulum.

U.S. Pat. No. 6,214,014 describes a system which uses a goniometer to engage with bone portions of the pelvis measure a reference angle. The system allows the surgeon to adjust the goniometer to a desired offset. A laser beam aligned with the goniometer is then fired at a wall and a mark made on the wall. The surgeon then removes the goniometer. The system includes an introducer having a laser mounted thereon. When the laser beam is aligned with the mark on the wall the introducer is correctly oriented.

None of the known techniques of orienting the prosthetic acetabular cup is satisfactory. The more complex and hence more accurate devices are physically large, resulting in cramped conditions in smaller operating theatres, and are expensive.

The more basic instrument aids give the orthopaedic surgeon some guidance beyond simply lining up the prosthetic acetabular cup by eye. However, they do not provide for the cup to position with reference to the position of the hip joint in the standing position.

The hip is designed to function with the person in the standing position. However, hip replacement operations are performed with the patient lying down, usually on his side, with the hip to be replaced uppermost. The position occupied by the pelvis when the patient is lying down is different to the position occupied by the pelvis when the person is standing.

It would be desirable to provide an apparatus that would allow the prosthetic acetabular cup to be oriented as closely as possible to the desired orientation.

The prosthetic acetabular cup must be oriented in two planes. With the patient in the standing position it is desirable that the face of the cup should be aligned at 45 degrees to the vertical and that the face of the cup should lie at approximately 15 degrees of antiversion with respect to a vertical plane extending through the femoral balls.

SUMMARY OF THE INVENTION

According to a first aspect of the invention there is provided a medical instrument.

According to a second aspect of the invention there is provided an apparatus.

According to a third aspect of the invention there is provided a method of providing a guide for use in the introduction of a prosthetic acetabular cup.

According to a third aspect of the invention there is provided an alignment device.

According to a fifth aspect of the invention there is provided a method of fitting a prosthetic acetabular cup into a pelvis.

BRIEF DESCRIPTION OF THE DRAWINGS

In the drawings, which illustrate preferred embodiments of the invention, and are by way of example:

FIG. 3a is a cross-sectional side view of a patient alignment instrument;

FIG. 3b is a plan view of the alignment instrument illustrated in FIG. 3a;

FIG. 4a is a front view of a prosthetic acetabular cup alignment instrument according to the invention;

FIG. 4b is a side view of the instrument illustrated in FIG. 4a;

FIG. 4c is a cross-sectional side view of a component of the instrument illustrated in FIGS. 4a and 4b;

FIG. 4d is a plan view of the first member of the instrument;

FIG. 4e is a side view of the third member of the instrument;

FIG. 7b is a front view of the prosthetic acetabular cup alignment instrument according to the invention illustrated in FIG. 7a;

FIG. 8a is a front view of a mounting element;

FIG. 8b is a side view of the mounting element illustrated in FIG. 8a;

FIG. 9a is a side view of an alternative embodiment of an alignment instrument; and FIG. 9b is a front view of the alignment instrument illustrated in FIG. 9a.

DETAILED DESCRIPTION OF THE PREFERRED EMBODIMENTS

Figure 1A:
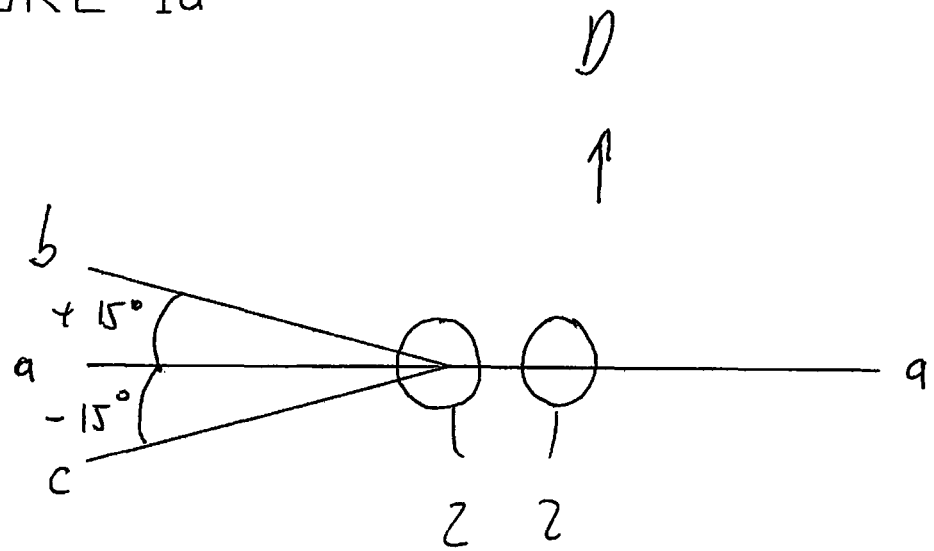
FIG. 1a is a cross-sectional plan view illustrating the datum axis for the measurement of anteversion.

FIG. 1a illustrates a cross-sectional plan view of a person facing in the direction indicated by arrow D. An anteversion datum axis is indicated by the broken line a-a lies on a vertical plane passing through the centre of a person's body, the legs 2 of which are shown. The anteversion datum axis is shown in order to define the meaning of anteversion in the present application. The line b has +15 degrees of anteversion, whereas the line c has −15 degrees of anterversion.

Figure 1B:
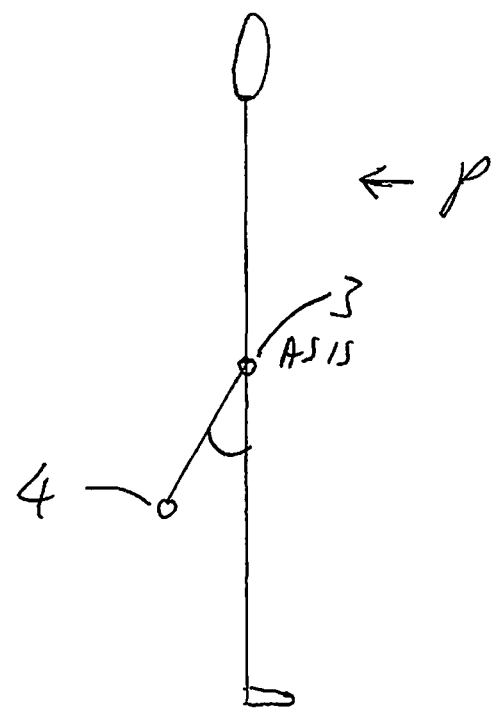
FIG. 1b is a side view of a patient illustrating the angle measured during a pre-operation X-ray.

Referring now to FIG. 1b, there is illustrated a patient P standing for a pre-operation X-ray. From this X-ray it is possible to measure the angle of a line passing through the anterior superior iliac spine (ASIS) 3 and the centre of rotation of the hip 4.

Hip replacement surgery is performed with the patient P lying on his side. When a person moves from the standing position in which the pre-operation x-ray is taken to the lying position in which the operation is performed, there is a change in the position of parts of the patient's skeletal structure. One of the functions of the apparatus of the invention is to correct for such changes.

A first step in the operation is to orient the patient so that the datum line a-a is oriented vertically. The patient's position on the operating table is manipulated manually and is measured using the alignment device illustrated in FIG. 3a.

The alignment device 10 comprises a rod 11 and mounted thereon a pair of spacers 14, each comprising an end plate 15 for engagement with an ASIS of the patient, and each attached to a respective mounting member 13 by means of a rod 16. The mounting members 13 are slidably mounted on the rod 11 and are each provided with a grub screw 17 which provides for the position of the mounting member 13 to be fixed with respect to the rod 11. The rod 16 may be extendible and retractable with respect to the mounting member 13. Preferably, where the rod is extendible and retractable with respect to the mounting member defined positioning means are provided in each rod 16 or mounting member 13, in order that the end plates are maintained in the same plane and parallel to the rod 11. For example, one of the rod 16 and mounting member 13 may be provided with a series of spaced apart holes 16', and means to engage those holes provided, such as a sprung ball that engages one of the holes, or a pin which passes through one of the holes and a hole in other of the rod 16 and the mounting member 13. Alternatively, the rods may be provided with markings as shown in FIG. 9a, which may be aligned with a wall of the mounting member 13. It is important that the two ASIS lie in a common vertical plane, therefore the plates 15 should lie in a common plane. It may however be desirable to provide for adjustment of the length of the rods 16 so that the alignment device can be used with patients of different size and shape.

A spirit level 12, which may be a two or three dimensional spirit level, is mounted on one end of the rod. In use, the device 10 is held so that the spirit level 12 indicates that the rod is lying vertically in all three planes where a three dimensional spirit level is used, and the position of the patient is manipulated such that each ASIS touches one of the end plates 15.

The patient P is then strapped to the operating table, the aim being to restrict movement of the patient with respect to the table after being established in the desired position. At this point the alignment device 10 is removed from the patient.

The next step in a hip replacement procedure where the apparatus of the invention is to be used involves attaching a bone screw to the ASIS. Typically, the surgeon would drill the hole in a direction substantially normal to the longitudinal axis of the patient P and the operating table. However, if the hole is not aligned with the normal it does not matter as the apparatus of the invention can accommodate any offset to the normal.

Referring now to FIG. 4a to 4d or 4h, which illustrate a prosthetic acetabular cup alignment instrument 20, which is mounted on a bone screw 21. In this embodiment of the invention the bone screw 21 is hexagonal in cross-section. In fact the bone screw may have any cross-sectional shape, although a non-circular shape is preferred so that rotation of the instrument about the screw is prevented. The bone screw could be square or round with a flat for example. The instrument 20 includes a member 22, which is configured to be slidably mounted on the bone screw 21, that is, the member 22 includes a bore 23, the bore 23 and the bone screw 21 having corresponding cross-sectional shapes.

The instrument 20 includes a means to lock the position of the member 22, and hence the instrument 20, with respect to the bone screw 21. In the illustrated example, the member includes a second bore 24, which is threaded and which intersects the first bore 23. A grub screw 25 engages with the internally threaded second bore 24. When turned in one direction and sufficiently, the free end of the grub screw 25 engages with the bone screw 21 and locks the position of the member 22, and hence the instrument 20, with respect to the bone screw 21.

The instrument 20 includes four members, each movable with respect to each other and lockable with respect to each other when desired alignments therebetween have been reached. The first member 22 includes a socket 26 of a ball and socket joint. The second member 30 includes a ball 31, which sits in the socket 26, the ball member 30 including a stub shaft 32 for engagement in a correspondingly shaped housing 41 in the third member 40. The ball member 30 further includes a shoulder element 33, the reverse side 34 of which presents a flat surface which extends around the shaft 32 and forms a flat face for abutment with an end face 44' of a wall element 44 of the third member 40.

Figure 4F:
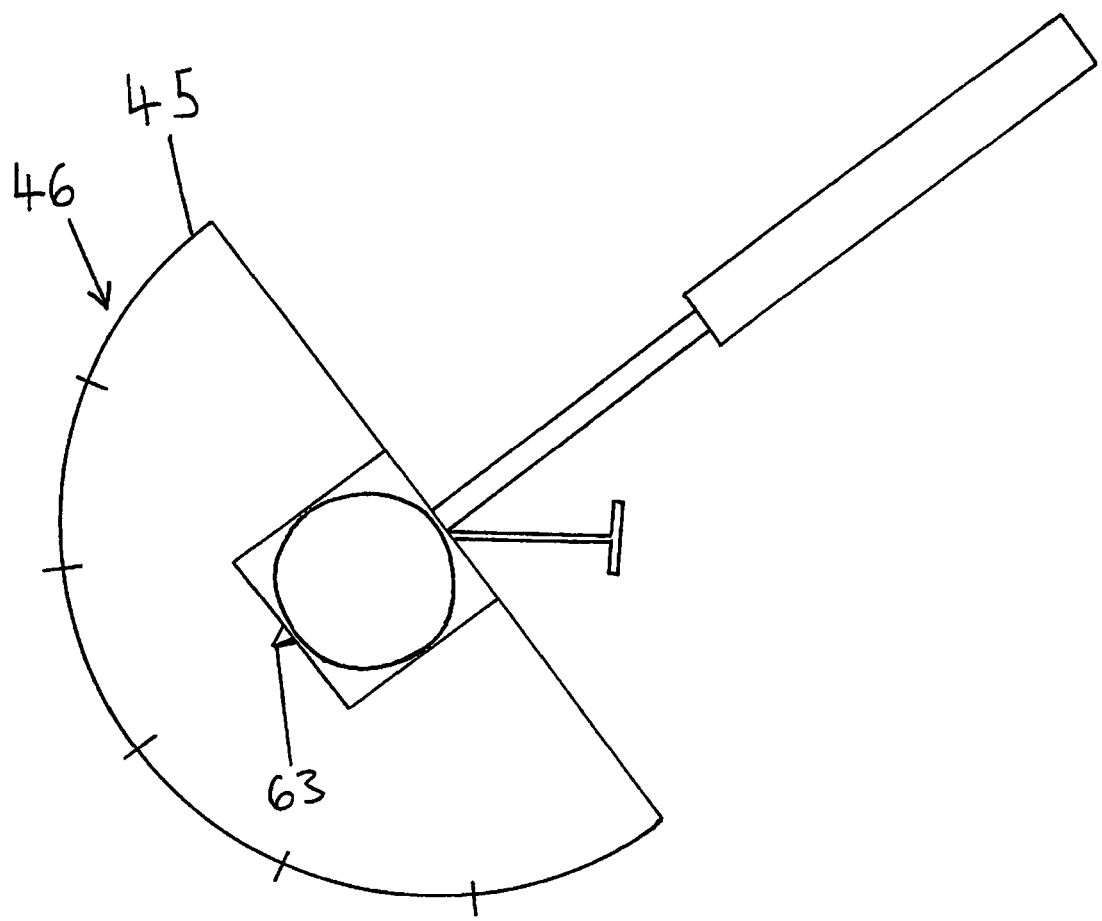
FIG. 4f is a plan view of the instrument illustrated in FIGS. 4a to 4c with the laser set to 0 degrees.
Figure 4G:
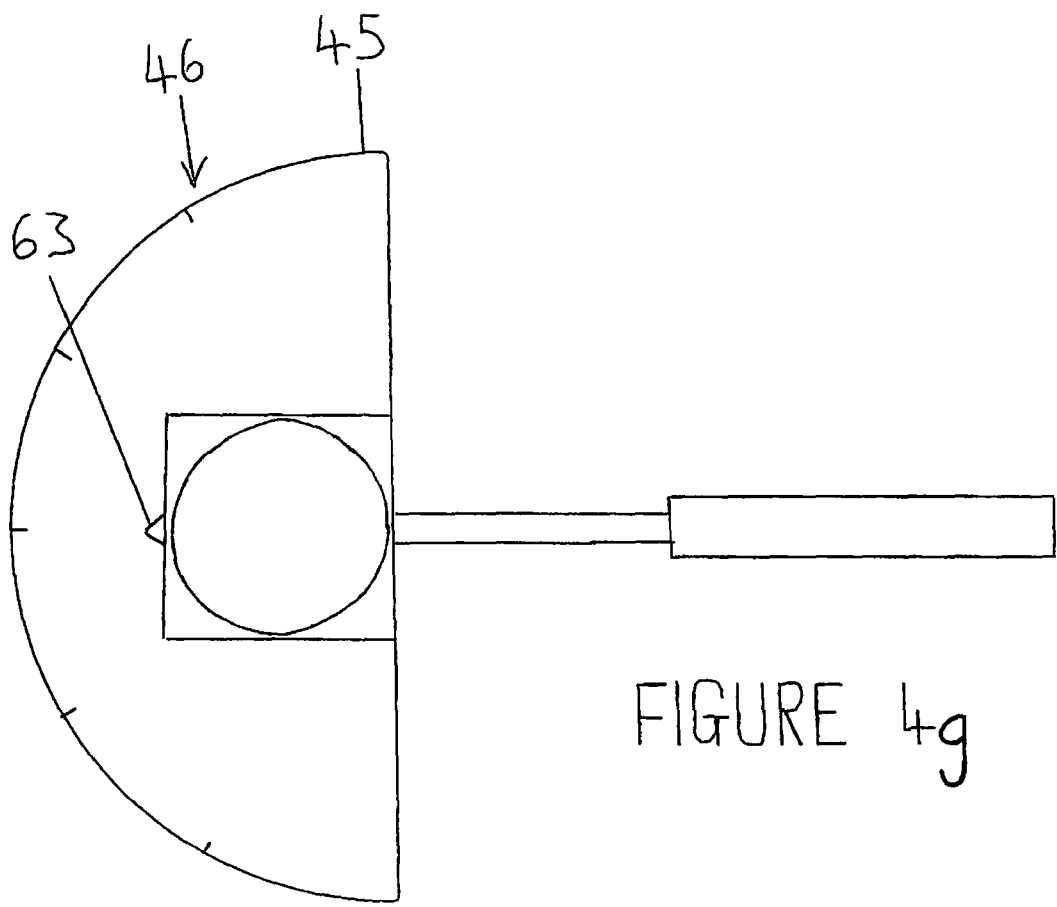
FIG. 4g is a plan view of the instrument illustrated in FIGS. 4a to 4d post alignment of a marker associated with the instrument with the centre of rotation of the hip.
Figure 4H:
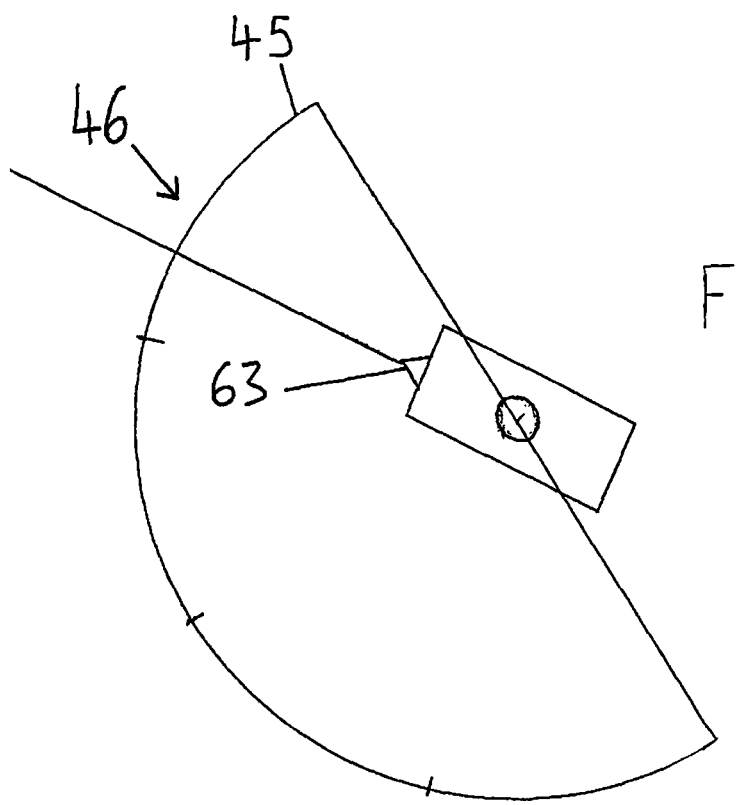
FIG. 4h is a plan view of the instrument illustrated in FIGS. 4a to 4e with the laser mount oriented to correspond to the angle X measured during the pre-operation X-ray and the desired angle of anteversion.

In the illustrated example, relative rotation between the first and second members is controlled by the configuration of the body of the member 22. As can be seen in FIGS. 4a and 4d, the first member includes a slot 22a. In the member 22 to either side of the slot are threaded bores 22b, 22c, these bores being aligned axially. A screw 22d engages with the bores 22b, 22c to tighten or slacken the member 22 on to or off the ball 31 of the second member 30.

The wall element 44 of the third member 40 includes a threaded bore 42, which receives a grub screw 43. The bore 42 extends into the housing 41 so that the end of the grub screw 43 may engage the outer surface of the stub shaft 32, so as to prevent rotation between the second and third members.

The third member 40 includes a calibration plate 45, which in the illustrated example is semi-circular, and is in fixed relationship to the wall 44 of said member 40. As can be seen from FIG. 4e, the calibration plate includes a scale 46. The central indication on the scale is of 0 degrees, with up to plus and minus 45 degrees being to either side of 0 degrees.

The third member 40 also mounts a lever arm 47 in a mounting recess 48. The lever arm 47 comprises two arm sections 47a, 47b joined together at a hinge 47c. One end of the arm section 47a is configured for mounting in the recess 48 and comprises part of an attachment means for attaching the arm section 47a to the recess 48. For example, the arm section 47a may include a protrusion 47d to engage with an indent 49 situated in a wall of the recess 48. Protrusions 47d may be provided on each side of the arm section 47a for engagement with indents 49 situated in opposing walls of the recess 48. The recess 48 is so shaped and dimensioned as to permit the arm section 47a to pivot about the axis extending through the indent(s) and protrusion(s). In conjunction with the hinge 47c, the distance of the free end of the arm section 47b to the point of attachment of the arm section 47a to the wall 44 may be adjusted.

In the illustrated example, the free end of the arm section 47b mounts an element in the form of a pin 47e.

The fourth member 60 is mounted on the third member 40 such that the fourth member 60 may rotate with respect to the third member 40. The third member 40 includes a bore 50 which receives a boss 62 extending from a body 61 of the fourth member 60. The boss 62 is a push fit into the bore 50. This provides that when the member 60 is rotated to a particular position with respect to the third member 40 the member 60 will be held in that position until a rotational force is again exerted on the fourth member 60.

The fourth member 60 mounts a number of components, in particular a pointer 63, a spirit level 64 and a direction indicator, which in the present example is a laser 65, but may be another form light beam or another form of electromagnetic radiation capable of indicating direction. The pointer 63 works in conjunction with the scale 46 to show the angle of orientation of the fourth member 60 with respect to the third member 40. The spirit level 64 is a three dimensional spirit level and is used to allow the combination of the second, third and fourth elements 30, 40, 60 to be position such that they lie vertically.

The laser 65 is mounted in a bore 65a which is formed in the body of the fourth member 60 such that when the fourth member is oriented vertically, the laser lies at a pre-defined angle of for example 45 degrees to the vertical. The laser 65 emits a laser beam 66.

The instrument may be provided with a number of different fourth members 60, each having the laser mounted such that it presents a different angle to the vertical. The need for such different fourth members will become apparent from the description below.

Figure 5:
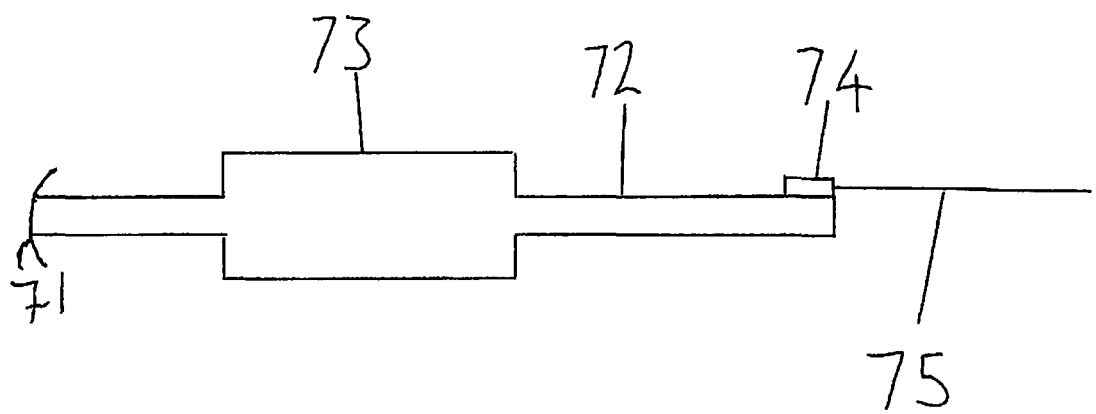
FIG. 5 is a schematic representation of an introducer suitable for use with the apparatus of the invention.
Figure 6:
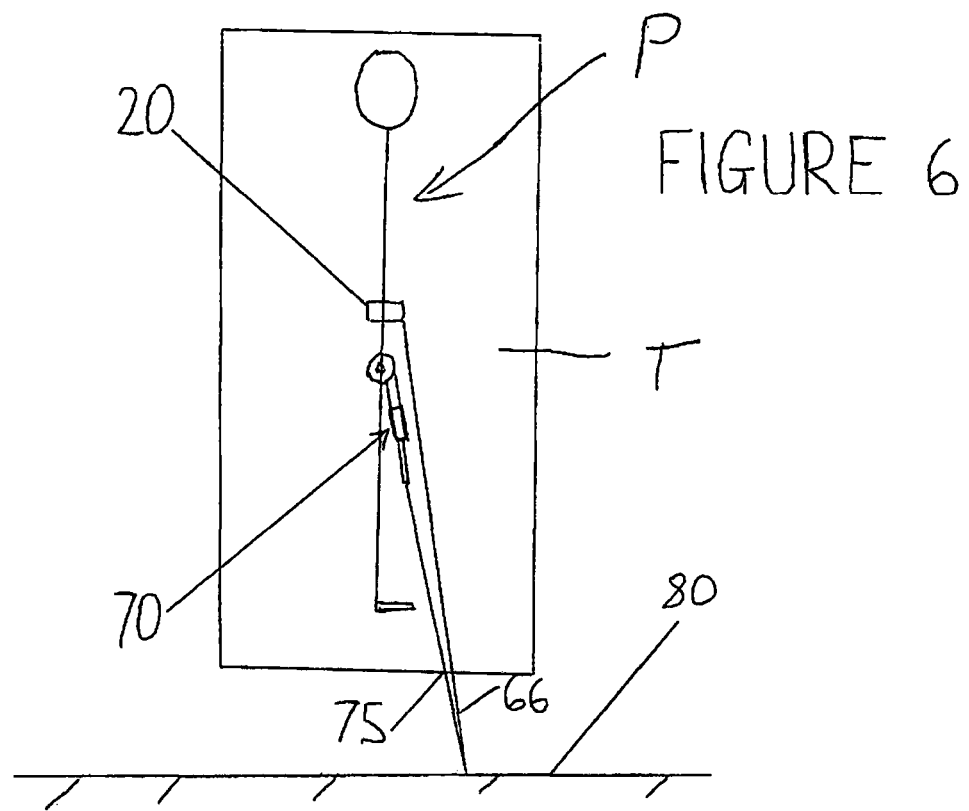
FIG. 6 illustrates the operating theatre and instruments being used just prior to insertion of the prosthetic acetabular cup.

Referring now to FIGS. 5 and 6, further components of the apparatus of the invention include an introducer 70 and a flat surface 80. An introducer is the tool used to introduce an acetabular cap into the socket of a hip joint. The introducer 70 includes a head 71 upon which an acetabular cap may be mounted, and a shaft 72. The shaft 72 mounts a grip portion 73 and a guide means in the form of a laser 74 for emitting a laser beam 75.

FIG. 6 illustrates an operating theatre in which a patient P is situated on an operating table T. The prosthetic acetabular cup alignment instrument 20 is attached to a patient and has been configured following the steps described below. The surgeon has placed a prosthetic acetabular cap onto the head 71 of the introducer 70. The laser 65 of the alignment instrument is switched on and emits a beam 66 which is incident on a flat surface 80 formed by a wall of the operating theatre. The laser 74 of the introducer is also switched on and emits a beam 75. The respective laser beams are aligned, at which point the surgeon may strike the end 72a of the shaft 72 to introduce the prosthetic acetabular cap into the socket of the hip joint.

The apparatus of the invention is used to provide the surgeon performing hip replacement surgery with accurate guidance for introducing a prosthetic acetabular cup.

The method of use of the apparatus of the invention will now be described below:

The first step in the method of the invention for inserting a prosthetic acetabular cup comprises taking an x-ray of the patient in the standing position side on to the hip upon which surgery is to be performed and on the x-ray measuring the angle x in FIG. 1b between the vertical and a line intersecting the ASSIS and the centre of rotation of the hip.

The second step in the method involves positioning the patient on the surface of the operating theatre with the hip upon which surgery is to be performed uppermost, and with the aid of the patient alignment instrument 10 illustrated in FIGS. 3a and 3b, adjusting the position of the patient until both ASIS lie in a common vertical plane.

The third step of the method involves drilling a hole in the uppermost ASIS and engaging a bone screw 21 in the so formed hole. It is preferred that the hole is drilled such that it lies in a substantially horizontal plane, and hence the bone screw 21 engaged in the hole also lies in a substantially horizontal plane. By drilling the hole in the horizontal plane, the maximum freedom of movement between the ball and the socket is preserved.

The fourth step of the method comprises mounting and securing the prosthetic acetabular cup alignment instrument 20 on the bone screw 21 by tightening the grub screw 25.

The fifth step of the method comprises slackening off screw 22*d* to release the ball and socket joint so that the ball 31 may move in the socket 26 and adjusting the orientation of the components mounted on the ball 31 until the three dimensional spirit level 64 indicates that the an axis passing through the spirit level 64 and the ball 31 lies vertically in two planes, and tightening the screw 22*d* to secure the position of the ball 31 with respect to the socket 26.

The sixth step of the method comprises rotating the member 60 such that marker 63 is aligned with the 0 degree indication on the scale 46 of the calibration plate 45.

Step seven of the method comprises moving the lever arm 47 such that the pointer 47*e* points at the centre of rotation of the acetabular cup. In general this involves rotation of the third member 40 with respect to the second member 30. When the pointer 47*e* is in the desired position the grub screw 43, thereby fixing position of the third member 40 with respect to the second member 30.

Step eight of the method comprises rotating the fourth member 60 with respect to the third member 40 through the measured angle X plus the desired degree of anteversion of the acetabular cup, which is typically about 15 degrees. With the first and second members locked together by virtue of the ball and socket being locked and the second and third members being locked together by virtue of the grub screw 43, the fourth member 60 may rotate with respect to the third member 40.

Step nine of the method comprises switching on the laser 65 such that the laser beam 66 shines on a wall of the operating theatre.

Step ten of the method comprises mounting a prosthetic acetabular cup on the head 71 of the introducer 70, and placing the acetabular cup in close proximity to the socket of the hip joint, and switching on the laser 74 such that the laser beam 75 shines on the same wall of the operating theatre.

Step eleven of the method comprises aligning the laser beam 66 with the laser beam 75 at the point on the wall where the two laser beams shine.

Step twelve comprises striking the free end of the shaft 72 of the introducer 70 to introduce the prosthetic acetabular cap into the socket of the hip joint.

Referring now to FIGS. 7*a* to 8*b*, there is shown an alternative embodiment of the invention. In this embodiment of the invention the ball of the ball and socket joint is part of the bone screw 21', with the socket part forming part of the instrument 20'.

The bone screw 21' comprises a threaded portion 21*a'* and a central portion of large cross-section 21*b'*, the two portions joined together by a chamfered wall 21*c'*. The bone screw 21' includes a ball 31', which is the ball of the ball and socket joint. The ball 31' is connected to the portion 21*b'* by a stem 21*d'*. The ball 31' includes a key 31*a'* for engagement by a tool, turning the tool causing the threaded portion to pull into or push out of a pre-drilled hole in the bone, as described above. The chamfered wall 21*c'* is advantageous as it provides a datum point. Engagement of the chamfered wall 21*c'* with the bone is the indication to the surgeon that the bone screw is correctly located in the bone. Whilst the surgeon could ascertain the depth of insertion of the threaded portion 21*a'* by eye or with other instrumentation or indica formed in the bone screw, the chamfered wall 21*c'* is particularly simple and effective.

The portion 21*b'* includes two bores 21*e'*, 21*f'*. The bores 21*e'*, 21*f'* are threaded internally, each having an opening 21*g'* in the side wall of the central portion 21*b'* and another opening 21*h'* in the chamfered wall 21*c'*. A grub screw inserted through the opening 21*g'* and rotated in one direction will exit through the opening 21*h'*. With the threaded portion 21*a'* screwed into the bone, the end of the grub screw will also engage the bone. This further secures the bone screw 21' in the bone, for example against a turning force generated by the weight of the instrument.

Figure 7A:
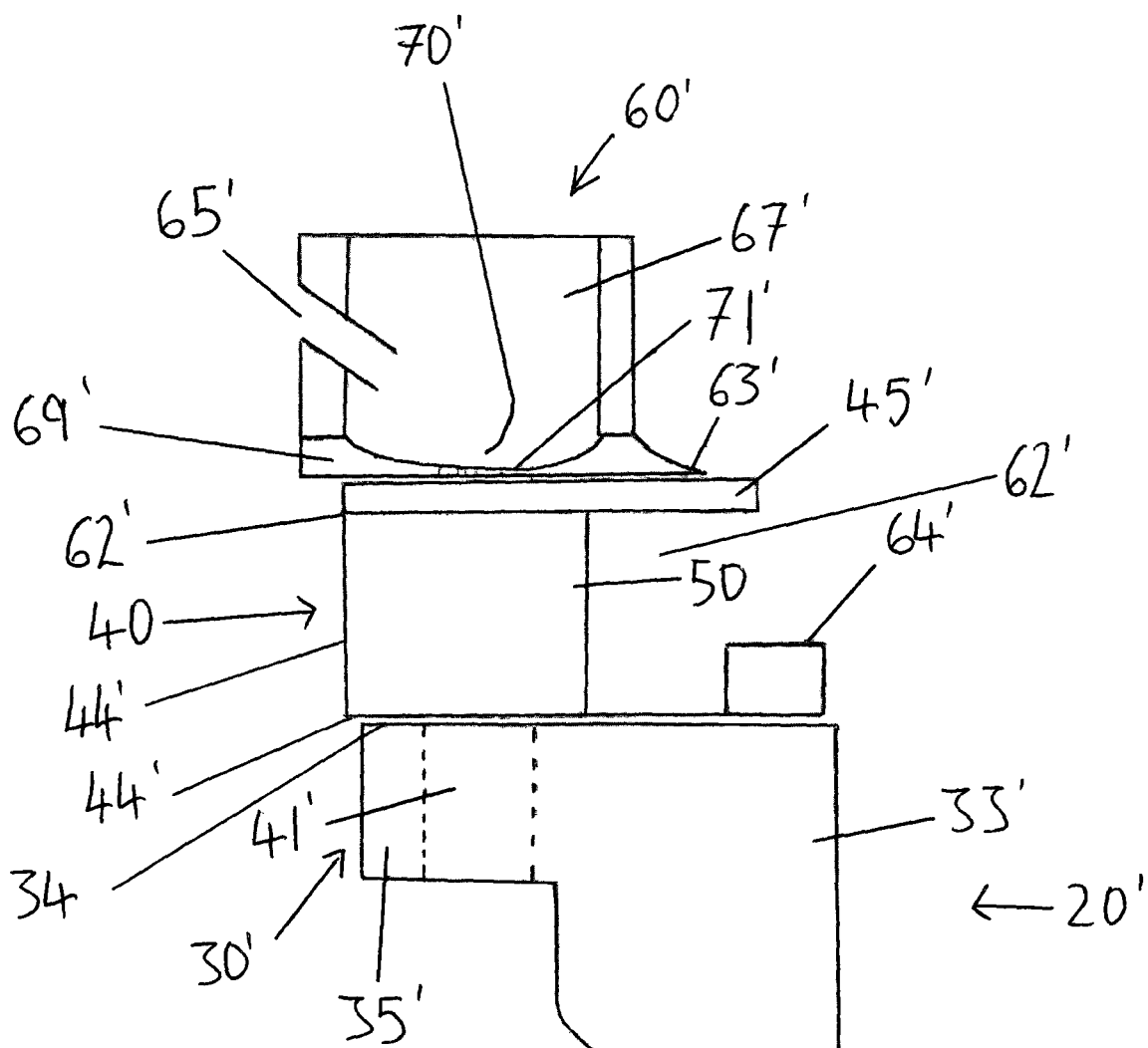
FIG. 7a is a side view of a prosthetic acetabular cup alignment instrument according to another aspect of the invention.

Referring specifically to FIGS. 7*a* and 7*b*, the instrument 20' includes five members.

The second member 30' includes a lower portion 22', which comprises the socket 26' for receiving the ball 31' forming the first member. The lower portion 22' includes a first part 22*b'* and a second part 22*c'*, which second part is mounted on the lower portion 22' by means of a hinge pin 22*e'*. A grub screw 22*d'* extends through a bore in the part 22*b'* into an aligned and internally threaded bore in the part 22*c'*. By slackening off or removing the grub screw 22*d'*, the second part pivots about the hinge pin 22*e'*, opening the socket 26' in order that the ball 31' may be inserted therein. The grub screw 22*d'* is turned in the opposite direction to secure the ball 31' in the socket.

The lower portion of the second member 30' is fixed with respect to the upper portion thereof, and the two portions may be formed in the same part.

The second member 30' comprises an upper portion which includes wall elements 35' that form a housing for receiving a stub shaft 41' of the third member 40. A grub screw 43' extends through bores in each of the wall elements 35', at least one of the bores being internally threaded in order that the grub screw may pull the wall elements 35' together to grip the stub shaft 41'.

A three dimensional spirit level 64' is mounted on an upper surface 34' of the upper portion 33'. The spirit level 64' is a three dimensional spirit level and is used to allow the combination of the second, third and fourth elements 30, 40, 60 to be position such that they lie vertically.

The third member 40', which is mounted to rotate in the second member 30'. The third member 40' includes a calibration plate 45', which in the illustrated example is semicircular, and is in fixed relationship to the wall 44' of said member 40'.

The calibration plate 45' includes the same scale and indicia as described above in relation to FIG. 4*e*.

Further, the third member 40' also provides a mounting recess 48' for mounting a lever arm in the same manner as described above in relation to FIG. 4*b*.

The fourth member 60' is mounted on the third 40' such that the fourth member 60' may rotate with respect to the third member 40'. The third member 40 includes a bore 50' which receives a boss 62' extending from a body 61' of the fourth member 60'. The boss 62' is a push fit into the bore 50'. This provides that when the member 60' is rotated to a particular position with respect to the third member 40' the member 60' will be held in that position until a rotational force is again exerted on the fourth member 60'.

The fourth member 60' mounts a pointer 63'. The pointer 63' works in conjunction with the scale 46' to show the angle of orientation of the fourth member 60' with respect to the third member 40'. Looking at FIG. 7b, it can be seen that the fourth member 60' is substantially L-shaped in cross-section, having a side wall 68' and a base wall 69'. The pointed 63' is formed as an integral part of the base wall 69'.

The fifth member 67' is mounted in the L-shaped fourth member as can be seen from both FIGS. 7a and 7b. The fifth member 67' is mounted on the fourth member 60' so as to rotate with respect thereto about an axis extending normal to the side wall 68'. The lower edge of the fifth member and the upper edge of the base wall 69' are correspondingly curved, and each are provided with indicia 70', 71'. In the present example, the indicia 71' provides markings at one degree intervals from zero representing vertical to ten degrees either side of vertical. The indica 70' is a single mark.

Figure 2A:
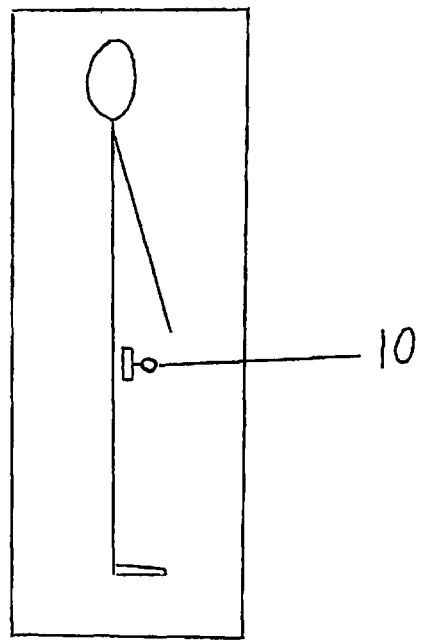
FIG. 2a is a plan view of a patient lying on an operating table during a part of a hip replacement procedure.
Figure 2B:
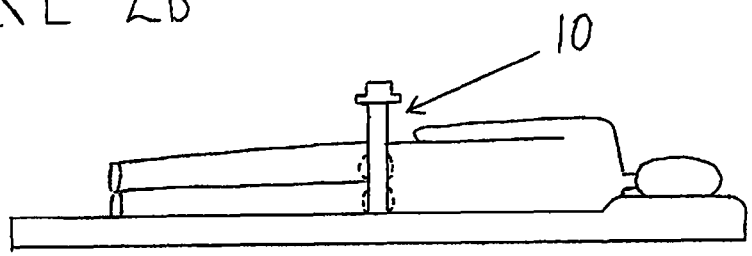
FIG. 2b is a front view of the patient lying on the operating table during another part of a hip replacement procedure.

In the present example, the FIG. 2b illustrates a vertical axis b-b. The pelvis may be tilted such that the axis b-b lies off vertical by up to 10 degrees either side of the vertical.

The fifth member 67' is mounted on the fourth member 60' so that when the fifth member 67' is rotated from a first position to a second position, it remains in the second position. For example, this may be due to friction between the adjacent walls of the fourth and fifth members, or the between a stub shaft of one of the members and a housing of the other.

The fifth member 67' mounts a laser 65', which is mounted in a bore 65a' which is formed in the body of the fifth member 67' such that when the fourth member is oriented vertically, the laser lies at a pre-defined angle of for example 45 degrees to the vertical, when the indicia 70' is aligned with the on vertical indicia 71', that is the centre most indicia. The laser 65' emits a laser beam 66'.

The additional adjustment provided for by the embodiment illustrated in FIGS. 7a and 7b by being able to rotate the part which mounts the laser about a horizontal axis will be described below. The fourth and fifth members need not be in the form illustrated in FIGS. 7a and 7b. What is important is that the fourth member may rotate about a first axis and the fifth member about an axis normal to the first axis. For example, the fifth member may be a simple as a direction indicator such as a laser mounted in a body, the body being rotatable about the aforementioned axis.

It should be noted that the fourth member of the embodiment illustrated in FIGS. 7a and 7b could be used with the embodiment shown in FIGS. 1 to 6. Further, the fourth member of the embodiment shown in FIGS. 1 to 6 could be used in place of the fourth member 60' shown in FIGS. 7a and 7b.

FIG. 2b illustrates a vertical axis b-b. The pelvis may be tilted such that the axis b-b lies off vertical by up to 10 degrees either side of the vertical. By mounting the laser 65' in the fifth member 67', such that it may rotate with respect to the fourth member 60' the degree of pelvic tilt may be compensated for.

The method of use of the apparatus illustrated in FIGS. 7 to 9 is essentially the same as the method of use of the apparatus illustrated in FIGS. 1 to 6. However, the step of aligning the alignment instrument involves aligning the axis a-a to the vertical, which may be achieved using the alignment instrument illustrated in FIGS. 9a and 9b. This alignment instrument provides for alignment to the vertical in only one plane, and is used to align the axis a-a to the vertical.

The method includes the first additional step of measuring the angle at which the axis b-b lies to the vertical and recording that angle. This step is performed between the second and third steps described above.

The method includes the second additional step of rotating the fifth member 67' with respect to the fourth member 60' through an angle corresponding to the angle formed by the axis b-b with the vertical. This step may be performed at any time between recording the angle of the axis b-b to the vertical and step 9 described above.

The third step is also modified. The bone screw 21' is rotated until the chamfered wall 21c' engages the bone. A grub screw is then inserted into one of the bores 21e', 21f', whichever has opening 21h' facing the bone, and that grub screw is tightened.

Clearly, the fourth and fifth steps are modified to reflect that the ball of the ball and socket joint is part of the bone screw.

The apparatus and method of the invention provide a simple yet accurate means of aligning the prosthetic acetabular cup correctly prior its introduction into the socket of the hip joint.

Features of one embodiment may replace equivalent features in another embodiment.

The invention claimed is:

1. A medical instrument comprising a mount attachable to a bone, and a plurality of members including first, second, third and fourth members, wherein second member is selectively rotatable with respect to the first member, the third member is selectively rotatable with respect to the second member, and the fourth member is selectively rotatable relative the third member, each of the selectively rotatable members being rotatable about a first axis extending in a first direction, and further comprising a connection that permits rotation between one of the said members and another about second and third axes, wherein the first, second, and third axes extend in directions which are orthogonal to one another, and wherein one of said members mounts a level and wherein one of said members mounts a direction indicator, and wherein one of the members includes a scale and an adjacent one of the members includes a scale position indicator.

2. A medical instrument according to claim 1, wherein the connection that permits rotation between one of said members and another about second and third axes is situated between the first and second members.

3. A medical instrument according to claim 1, wherein the connection that permits rotation between one of said members and another comprises a universal joint, one side of the universal joint being associated with one of said members and another side of the universal joint being associated with an adjacent one of said members.

4. A medical instrument according to claim 1, wherein the first member is part of the mount attachable to a bone.

5. A medical instrument according to claim 1, comprising locking means adapted to lock the position of the members to each side of the universal joint in a selected position.

6. A medical instrument according to claim 5, wherein the universal joint is a ball and socket joint, wherein the ball is associated with one of said members and the socket with an adjacent one of said members and the locking means includes a screw, and wherein rotation of the screw in one direction engages the ball and socket together to lock said ball and socket in a desired position, and wherein rotation of the screw in an opposite direction disengages the ball and socket thereby permitting movement therebetween.

7. A medical instrument according to claim 6, wherein the member in which the socket is formed includes two portions separated by a gap, and aligned bores in each of the two portions configured to receive the screw, at least one of the bores being internally threaded, wherein rotation of the screw in one direction closes the gap to lock the position of the ball with respect to the socket, and wherein rotation of the screw in the other direction permits the gap to open, to permit movement of the ball with respect to the socket.

8. A medical instrument according to claim 1, comprising means to hold each of the four members in a selected position post rotation of one member with respect to another.

9. A medical instrument according to claim 8, wherein the means to hold one of the four members in a selected position with respect to another is provided by at least one of: an element passing through a part of one of the members and engaging with a part of an adjacent member, adjacent surfaces of adjacent parts engaging one another, and the fit of a shaft part of one of the members in a bore part of an adjacent one of the members.

10. A medical instrument according to claim 1, further comprising a lever attached to one of the members.

11. A medical instrument according to claim 10, wherein the lever is pivotally attached to said member one of the members.

12. A medical instrument according to claim 10, wherein the said one of the members includes a recess having walls and an end of the lever fits into the recess, wherein one of the lever and the recess includes protrusions and the other includes indents, wherein the protrusions engage with the indents to pivotally attach together the lever and the member.

13. A medical instrument according to claim 10, wherein the lever mounts a pointer at its end distal from the member to which it is attached.

14. A medical instrument according to claim 13, wherein the pointer is connected to the lever by a hinge.

15. A medical instrument according to claim 10, wherein the lever includes at least two lever arms, wherein the lever arms are joined together by a hinge.

16. A medical instrument according to claim 1, wherein the level includes a spirit level.

17. A medical instrument according to 16, wherein the level is mounted on one of the second, third or fourth members.

18. A medical instrument according to claim 1, wherein the level and the direction indicator are mounted on the same one of the four members.

19. A medical instrument according to claim 1, wherein the direction indicator is mounted such that the direction indicated is at a fixed angle relative to the first axis.

20. A medical instrument according to claim 19, wherein the fixed angle is 45 degrees.

21. A medical instrument according to claim 1, wherein the direction indicator is a light beam emitter.

22. A medical device according to claim 1, wherein the plurality of members includes a fifth member adapted to rotate about a plane normal to the first axis.

23. A medical instrument according to claim 22, wherein the fifth member and an adjacent one of the other members are provided with indicia, configured to indicate the extent of rotation of the fifth member.

24. A medical instrument according to claim 22, wherein the fifth member is mounted on the fourth member.

25. A medical instrument according to claim 24, wherein the direction indicator is mounted in the fifth member.

26. A medical instrument according to claim 23, wherein the direction indicator is mounted such that the direction indicated is an angle of 45 degrees with zero rotation of the fifth member about the plane normal to the first axis.

27. A medical instrument according to claim 1, wherein the mount comprises a bone screw having a threaded portion for engagement with a bone.

28. A medical instrument according to claim 27, further comprising a shaft for engagement with a correspondingly shaped bore of one of said members.

29. A medical instrument according to claim 28, wherein the shaft and the bore are shaped so as to prevent rotation therebetween.

30. A medical instrument according to claim 27, wherein the mount includes at least one bore lying at an angle to the longitudinal axis of the bone screw, the bore adapted to receive a grub screw.

31. A medical instrument comprising:
a mount attachable to a bone, and first, second, third and fourth members, wherein the second member is selectively rotatable with respect to the first member, the third member is selectively rotatable with respect to the second member, and the fourth member is selectively rotatable to the third member, each selectively rotatable member rotatable about a first axis extending in a first direction; and
a connection that permits rotation between one of the said members and another about second and third axes;
wherein one of said members mounts a level and one of said members mounts a direction indicator; and wherein one of the members includes a scale and an adjacent one of the members includes a scale position indicator;
wherein the connection that permits rotation between one of said members and another about second and third axes connects the first and second members; and
wherein the mount comprises a bone screw having a threaded portion for engagement with a bone, and one part of the connection that permits rotation between one of said members and another about the second and third axes.

32. A medical instrument according to claim 31, wherein one part of the connection that permits rotation between one of said members and another about the second and third axes is one of a ball and socket of a ball and socket joint.

33. Apparatus comprising a medical instrument according to claim 1 and an introducer, the introducer having a direction indicator mounted thereon.

34. A medical instrument according to claim 33, wherein the direction indicator is a light emitting beam.

* * * * *